United States Patent [19]
Griesbach et al.

[11] Patent Number: 6,055,987
[45] Date of Patent: May 2, 2000

[54] SURGICAL DRAPE AND SURGICAL DRAPE KIT

[75] Inventors: Henry L. Griesbach, Atlanta; Richard C. Dowdy, Duluth; Gregory S. Hafer, Roswell, all of Ga.

[73] Assignee: Kimberly-Clark Wordwide, Inc., Neenah, Wis.

[21] Appl. No.: 09/001,523

[22] Filed: Dec. 31, 1997

[51] Int. Cl.$^7$ .................................................. A61B 19/00
[52] U.S. Cl. ........................................... 128/849; 128/852
[58] Field of Search ..................................... 128/849–856

[56] References Cited

U.S. PATENT DOCUMENTS

| | | |
|---|---|---|
| 3,849,241 | 11/1974 | Buntin et al. . |
| 3,855,046 | 12/1974 | Hansen et al. . |
| 3,881,474 | 5/1975 | Krzewinski . |
| 4,041,203 | 8/1977 | Brock et al. . |
| 4,379,192 | 4/1983 | Wahlquist et al. . |
| 4,957,120 | 9/1990 | Grier-Idris . |
| 5,010,899 | 4/1991 | Thompson . |
| 5,345,946 | 9/1994 | Butterworth et al. . |
| 5,388,593 | 2/1995 | Thomalla . |
| 5,418,045 | 5/1995 | Pike et al. . |
| 5,540,979 | 7/1996 | Yahiaoui et al. . |

*Primary Examiner*—Michael A. Brown
*Attorney, Agent, or Firm*—Dority & Manning P.A.

[57] ABSTRACT

A surgical drape and surgical drape kit are provided for engaging a hook fastener to fasten the surgical drape to an object. The surgical drape comprises a fabric including a nonwoven layer, the nonwoven layer having a surface including a plurality of strands. The strands are arranged on the surface with a plurality of bonds spaced about the surface and a plurality of loops extending between the bonds, the loops being engageable with the hook fastener for fastening the surgical drape to the object. The surgical drape kit may also comprise a plurality of surgical drapes for use together during a surgical procedure, the loops being engageable with the hook fastener for fastening the surgical drapes together.

30 Claims, 4 Drawing Sheets

SURGICAL DRAPE AND SURGICAL DRAPE KIT

BACKGROUND OF THE INVENTION

The present invention relates to an improved surgical drape and surgical drape kit, and more particularly relates to a surgical drape suitable for use with positionable fasteners and to a surgical drape kit including positionable fasteners, allowing medical personnel greater flexibility in positioning and repositioning the drape and/or surgical tools during a medical procedure.

Various types of surgical drapes have been used to keep a surgical site on a patient sterile during a surgical procedure. Traditionally, surgical drapes were linen or woven cloth, and were sterilized after each use for reuse. More recently, disposable drapes have been introduced, in which nonwoven paper or fabric forms a substantial part of the drape. A reinforcement area is often placed around a fenestration opening or edge in disposable surgical drapes to provide structural strength and to absorb bodily fluids from a surgical site. Many disposable drapes include a number of layers of different materials for the drape area and reinforcement area, with each layer providing a different property to the drape. For example, spunbond fabrics, meltblown fabrics, and polymer films have been used as layers in disposable drapes.

Many different shapes of surgical drapes have been proposed, often depending upon the specific surgical procedure to be performed. For example, the shape of the drape was often specifically designed to fit around a specific surgical site on the body. In some cases, a fenestration opening was provided through a drape to allow medical personnel access to the surgical site, whereas the remaining sheet portion of the drape would cover the rest of the body and table. Often, several drapes were used in combination to cover a patient. In some cases, several rectangular drapes, often called universal drapes, were laid over the patient in a pattern providing an opening through which the medical personnel could access the surgical site while also covering the remainder of the patient's body and the table.

Various structures have been developed to attach surgical drapes or portions of drapes together. For example, U.S. Pat. No. 4,957,120 discloses a surgical drape including a pouch attached to the drape. The pouch may be attached by using releasable fastening systems such as those that include snap or VELCRO® fastener components. One part of the releasable fastening system is mounted on the drape and the complimentary part (of the releasable fastening system) is mounted on the pouch. Thus, because the drape material itself was not suitable for direct connection to a fastening component such as a VELCRO® hook fastener, complimentary elements must be attached to both joined portions. Similarly, U.S. Pat. Nos. 5,338,593, 5,010,899, and 5,345,946 disclose surgical drapes where one or both components of an attachment system, such as VELCRO® hook fasteners and a complimentary loop material that engages the hook fastener, may be attached to a drape for attaching the drape to another drape, the surgical table, etc. In many of these systems, adhesive or snaps are disclosed as alternatives to the VELCRO® hook fastener and the loop material.

In all the above patents, at least one component of the fastening system, be it a snap, VELCRO® hook fastener, etc., is attached to the drape or portion. Thus, this element must be added to the drape material during manufacture. The added element must be sized properly and must be placed properly in order to work in conjunction with the complimentary fastening element as desired. In situations where adhesive is used, it is typically attached to one drape of a pair to be attached. However, adhesive is not suitable for repeated positioning, and only the portion of the drape including the adhesive is fastenably positionable.

In situations where snap elements or VELCRO® hook fasteners and loop materials are used, each component of the fastening system must be respectively placed on the drapes (or portions) that are to be attached. Both corresponding components of the fastening system must be located properly on the drapes (or portions), and the fastening elements only connect the drapes or portions in one given orientation. Therefore, the attachment systems disclosed in the above patents work for their desired purposes of creating a connected drape system, but the systems are limited to only providing the connected drapes in one orientation and do not provide flexibility or adjustability.

U.S. Pat. No. 3,881,474 discloses a surgical drape that employs tabs that may be used to fasten surgical tools in place during a surgical procedure. The tabs are attached to the drape adjacent a reenforcement area around a fenestration opening on the drape. The tabs are attached at specific places between the reinforcement area and the drape and are not movable or adjustable. The tabs include holes through which surgical tools or a securing cord may be passed. Applicants understand that, in practice, medical personnel often simply use a clamp to secure a surgical tool to such a tab or to the drape itself, rather than expending the time and effort to loop the surgical tools through the holes or to tie them down using a securing cord. Furthermore, recent surgical advances have increased the number of surgical tools extending into a surgical site in many operations, thus compounding the complexity of the use of such a tab system.

U.S. Pat. No. 5,010,899 discloses a surgical drape including a plurality of binding strips of material attached to the upper surface of the drape for maintaining medical devices during a surgical procedure. The strips may include a fastening system that uses VELCRO® hook fasteners and an engageable loop material or an adhesive strip for sealing the strip over onto itself. The strips are limited to a single placement on the drape and thus do not provide flexibility or adjustability, especially in view of the demands of newer surgical procedures and tools.

Because the loops and tabs of the above patents are limited to a given set position on their respective drapes, different drapes must be designed for different surgical procedures on different parts of the body. Therefore, hospitals must stock numerous drape sets to cover different surgical possibilities. Similarly, because drape connection is limited by the position of the connectors, the hospitals must maintain a stock of various drape sets. The manufacture, purchase, and inventory of numerous drapes and drape sets by hospitals can be extremely expensive. Furthermore, as new surgical procedures are developed, new drape designs may be required. Since drape design typically follows the surgical advance, specifically-designed drapes may not be immediately available for new surgical procedures.

OBJECTS AND SUMMARY OF THE INVENTION

It is a principle object of the present invention to provide an improved surgical drape and surgical drape kit that can be readily adapted to various applications.

Another object of the present invention is to provide an improved surgical drape and surgical drape kit that are simple and inexpensive to manufacture, and that are reliable in use.

Still another object of the present invention is to provide a surgical drape and surgical drape kit that allow for reduction of hospital costs related to purchasing and inventorying various drape and drape kit designs.

Yet another object of the present invention is to provide a surgical drape and surgical drape kit that allow for infinite positioning and repositioning of surgical tools and drapes to provide flexibility to surgical personnel.

Another object of the present invention is to provide a surgical drape and surgical drape kit that can be used by medical personnel performing new procedures for which specific surgical drapes have not yet been designed, or that eliminates the need for the specific design entirely.

Still another object of the present invention is to provide a surgical drape and surgical drape kit providing reliable securing of surgical tools around a surgical site.

Yet another object of the present invention is to provide a surgical drape and surgical drape kit that can be used in situations where a plurality of drapes are to be connected without requiring individual connectors to be pre-applied to all individual drapes.

Another object of the present invention is to provide a surgical drape and surgical drape kit that simplifies manufacture by reducing or eliminating the number of additional parts to be attached to individual drapes.

To achieve these objects, and in accordance with the purposes of the invention, as embodied and broadly described herein, a surgical drape is provided for engaging a hook fastener to fasten the surgical drape to an object, the drape comprising a fabric including a nonwoven layer, the nonwoven layer having a surface including a plurality of strands, the strands being arranged on the surface with a plurality of bonds spaced about the surface and a plurality of loops extending between the bonds, the loops being engageable with the hook fastener for fastening the surgical drape to the object.

The surgical drape may include a base sheet, the fabric forming substantially the entire base sheet. Alternately, the surgical drape may further include a base sheet, the fabric being secured to the base sheet, and the base sheet may define a surface area, and the fabric covering only a portion of the surface area.

In accordance with a second embodiment of the invention, a surgical drape kit comprises a surgical drape including a fabric having a nonwoven layer, the nonwoven layer having a surface including a plurality of strands, the strands being arranged on the surface with a plurality of bonds spaced about the surface and a plurality of loops extending between the bonds. A hook fastener includes a plurality of hooks for engaging the loops for fastening the surgical drape to an object.

Preferably, hook peel strength, measured between the hook fastener and the contacted drape surface, is about 100 g or more, and more preferably is about 110 g or more. Also, the hook shear strength, measured between the hook fastener and the contacted drape surface is preferably 1350 g or more, and more preferably is 2000 g or more.

Optionally the hook fastener may be formed integral with the fabric, and the fabric may include at least one slit defining at least one tab having a distal end, the hook fastener being disposed at the distal end of the tab. Alternately, the hook fastener may be formed separate from the fabric. If desired, the surgical drape kit may include a plurality of hook fasteners.

In accordance with another embodiment of the invention, a surgical drape is provided for engaging a hook fastener to fasten the surgical drape to an object, the surgical drape comprising a base sheet having a surface area, and a fabric including a nonwoven layer. The fabric is secured to the base sheet and has a surface area smaller than the surface area of the base sheet, the nonwoven layer having a surface including a plurality of strands. The strands are arranged on the surface with a plurality of bonds spaced about the surface and a plurality of loops extending between the bonds, the loops being engageable with the hook fastener for fastening the surgical drape to the object.

Optionally, the base sheet defines an edge, and the fabric is disposed adjacent the edge. Also, if the base sheet defines a fenestration opening, the fabric may be disposed adjacent or around the fenestration opening.

In accordance with another embodiment of the invention, a surgical drape kit comprises a surgical drape including a base sheet having a surface area and a fabric including a nonwoven layer, the fabric being secured to the base sheet and having a surface area smaller than the surface area of the base sheet, the nonwoven layer having a surface including a plurality of strands, the strands being arranged on the surface with a plurality of bonds spaced about the surface and a plurality of loops extending between the bonds. A hook fastener includes a plurality of hooks for engaging the loops for fastening the surgical drape to an object.

In accordance with another embodiment of the invention, a surgical drape kit is provided for use with a hook fastener, the drape kit comprising a plurality of surgical drapes for use together during a surgical procedure, the surgical drapes including a fabric including a nonwoven layer, the nonwoven layer having a surface including a plurality of strands, the strands being arranged on the surface with a plurality of bonds spaced about the surface and a plurality of loops extending between the bonds, the loops being engageable with the hook fastener for fastening the surgical drapes together.

In accordance with another embodiment of the invention, a surgical drape kit comprises a plurality of surgical drapes for use together during a surgical procedure, the surgical drapes including a fabric having a nonwoven layer, the nonwoven layer having a surface including a plurality of strands, the strands being arranged on the surface with a plurality of bonds spaced about the surface and a plurality of loops extending between the bonds. A hook fastener includes a plurality of hooks for engaging the loops for fastening the surgical drapes together. The hook fastener may be formed integral with or separate from the fabric.

Additional objects and advances of the invention will be set forth in part in the following description, or may be obvious from the description, or may be learned through the practice of the invention.

BRIEF DESCRIPTION OF THE DRAWINGS

The present invention will be more fully understood from the following detailed description, taken in conjunction with the accompanying drawings, wherein like reference numerals refer to like parts, and in which.

DETAILED DESCRIPTION OF THE PREFERRED EMBODIMENTS DEFINITIONS

As used herein the following terms have the specified meanings, unless the context demands a different meaning, or a different meaning is expressed; also, the singular generally includes the plural, and the plural generally includes the singular unless otherwise indicated.

"Nonwoven" means a web or fabric of fibers or filaments that is formed by means other than knitting or weaving and that contains bonds between some or all of the fibers or filaments; such bonds may be formed, for example, by thermal, adhesive or mechanical means such as entanglement.

"Fiber" means an elongated strand of defined length, such as staple fibers formed by cutting a continuous strand into lengths of, for example, 2 to 5 cm. Collections of fibers may have the same or different lengths.

"Filament" means a generally continuous strand that has a very large ratio of length to diameter.

"Strand" means either a fiber or a filament. "Spunbond" means a nonwoven web or fabric of filaments formed by melt extrusion of a polymer into strands that are quenched and drawn, usually by high velocity air, to strengthen the filaments which are collected on a forming surface and bonded, often by the patterned application of heat and pressure. Spunbonded processes are described, for example, in the following patents to which reference may be made for additional details: U.S. Pat. Nos. 4,340,563, 3,802,817, and 3,692,618.

"Meltblown" means a nonwoven web or fabric of fibers formed by extruding a molten thermoplastic material through a plurality of fine, usually circular, die capillaries as molten threads or filaments into converging high velocity, usually hot, gas streams which attenuate the filaments of molten thermoplastic material to reduce their diameter, which may be to microfiber diameter. Thereafter, the meltblown fibers are carried by the high velocity gas stream and are deposited on a collecting surface to form the web of randomly disbursed meltblown fibers. Such a process is disclosed, for example, in U.S. Pat. No. 3,849,241.

"Loop" means an area of separation of at least one fiber or filament from others in a nonwoven and includes but is not limited to configurations where the same fiber or filament intersects itself. Thus, in a loop, a complete circle or oval, for example, need not be formed.

"Hook" means a structure adapted for use as a mechanical fastener component and having projections of a profile, height, density, geometry and orientation so as to releasably attach to a loop portion of a nonwoven and provide the intended level of engagement to a loop material as measured by hook peel and shear strength tests (described in Test Procedures section). The projections need not be in the actual form of a hook, but may have other configurations, such as a mushroom shape, for example. Suitable hook materials may be unidirectional or bidirectional, and often comprise from about 16 to about 620 hooks per square centimeter and hook heights of from about 0.00254 cm to about 0.19 cm. They are available, for example, from Velcro International of Manchester, NH and 3M Corp. of St. Paul, Minn.

"Hydrophilic" describes fibers, filaments, or their surfaces that are wetted when contacted by aqueous liquids.

"Hydrophobic" describes fibers, filaments, or their surfaces that are not wetted when contacted by aqueous liquids.

"Layer" when used in the singular can have the dual meaning of a single element or a plurality of elements.

"Thermal point bonding" involves passing a fabric or web of fibers to be bonded between a heated calendar roll and an anvil roll. The calendar roll is usually patterned in some way so that the entire fabric is not bonded across its entire surface, and the anvil roll is usually smooth. As a result, various patterns for calendar rolls have been developed for functional as well as aesthetic reasons. One example of a pattern has points and is the Hansen-Pennings or "H&P" pattern with about a 30% bond area with about 200 pins/square inch as taught in U.S. Pat. No. 3,855,046. The H&P pattern has square point or pin bonding areas. Another typical point bonding pattern is the expanded Hansen-Pennings or "EHP" bond pattern which produces a 15% bond area. Another typical point bonding pattern designated "714" has square pin bonding areas wherein the resulting pattern has a bonded area of about 15%. Other common patterns include a diamond pattern with repeating and slightly offset diamonds with about a 16% bond area and a wire weave pattern looking as the name suggests, e.g. like a window screen, with about an 18% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

"Pattern unbonded" or interchangeably "point unbonded" or "PUB," means a fabric pattern having continuous thermally bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material of this invention includes providing a nonwoven fabric or web, providing opposedly positioned first and second calendar rolls and defining a nip therebetween, with at least one of the rolls being heated and having a bonding pattern on its outermost surface comprising a continuous pattern of land areas defining a plurality of discrete openings, apertures, or holes, and passing the nonwoven fabric or web within the nip formed by the rolls. Each of the openings in the roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in the roll or rolls forms a continuous pattern of bonded areas that define a plurality of discrete unbonded areas on at least one surface of the nonwoven fabric or web. Alternative embodiments of the process include pre-bonding the nonwoven fabric or web before passing the fabric or web within the nip formed by the calender rolls, or providing multiple nonwoven webs to form a pattern-unbonded laminate. The point unbonded pattern and process are described in U.S. patent application Ser. No. 08/754,419.

Test Procedures

Basis Weight: the basis weights of various materials described herein were determined in accordance with Federal Test Method No. 191A/5041.

Hook Peel Strength: the hook peel strength test involves attaching a hook material to a loop material of a hook and loop fastening system and then peeling the hook material from the loop material at a 180° angle. The maximum (or peak) load is recorded in grams as the peak load value measured to disengage or peel apart the two components, in this case the top surface of a drape or drape portion (the loop component) and the hook fastening strip (the hook component), during one test iteration. The test uses a continuous rate of extension tensile tester, such as a Sintech System 2 Computer Integrated Testing System, using a 5000 gram full scale load, available from Sintech, Inc., of Research Triangle Park, N.C. Samples of the loop material are cut into 3 inch (7.6 cm) by 6 inch (15.2 cm)sections. A 2.5 inch (6.3 cm) by 3.9 inch (10.0 cm) sample of a hook fastening strip is used having its ends covered with adhesive tape so that only a 1.5 inch (3.8 cm) central portion of the hook fastening strip is exposed. The exposed portion of the hook fastener is positioned hook side down and applied to the top surface of the loop material with about 1.0 inch (2.5 cm) overlap from the edge of the loop material. The samples of the loop material are cut to give samples extending in either the machine direction or the cross machine direction. Each of these samples is positioned with respect to the hook fastening strip so that the hook elements engage the loop material's surface in orthogonal directions. The tensile tester is activated at a constant rate of separation of 500 mm per minute, and the instantaneous load in grams to disengage or peel the hook fastening strip from the loop material cut in the machine and cross machine directions (at a 180° angle) is recorded respectively, and the highest load for each direction is recorded as the maximum (or peak) load.

Hook Shear Strength: after attaching the hook and loop components together, the shear strength is measured by pulling the hook component across the surface of the loop component. The maximum load is recorded in grams as the highest value needed to disengage or pull the two components, in this case the top surface of the drape or drape portion (the loop component) and the hook fastening strip (the hook component), apart. The test uses a continuous rate of extension tensile tester, such as a Sintech System 2 Computer Integrated Testing System, using a 5000 gram full scale load, available from Sintech, Inc., of Research Triangle Park, N.C. Samples of the loop material are cut into 3 inch (7.6 cm) by 6 inch (15.2 cm) sections. A 2.5 inch (6.3 cm) by 3.9 inch (10.0 cm) sample of hook fastening strip having its ends covered with adhesive tape so that only a 1.5 inch (3.8 cm) central portion of hook is used. The exposed section of the hook fastener is positioned hook side down and applied to the top surface of the loop material about 2.0 inches (5 cm) from the edge of the loop material in the test direction. The samples of the loop material are cut to give samples in either the machine direction or the cross machine direction. Each of these samples are positioned with respect to the hook fastening strip so that the hook elements engage the loop material's surface in orthogonal directions. The tensile tester is activated at a crosshead speed of 250 mm per minute, and the peak load in grams to disengage or pull the hook strip across the loop samples cut with a machine direction and cross machine direction orientation (at a 180° angle) is recorded respectively.

Reference will now be made in detail to the presently preferred embodiments of the invention, one or more examples of which are illustrated in the drawings. Each example is provided by way of explanation of the invention and not meant as a limitation of the invention. For example, features illustrated or described as part of one embodiment or figure can be used on another embodiment or figure to yield yet another embodiment. It is intended that the present invention include such modifications and variations.

Figure 1:
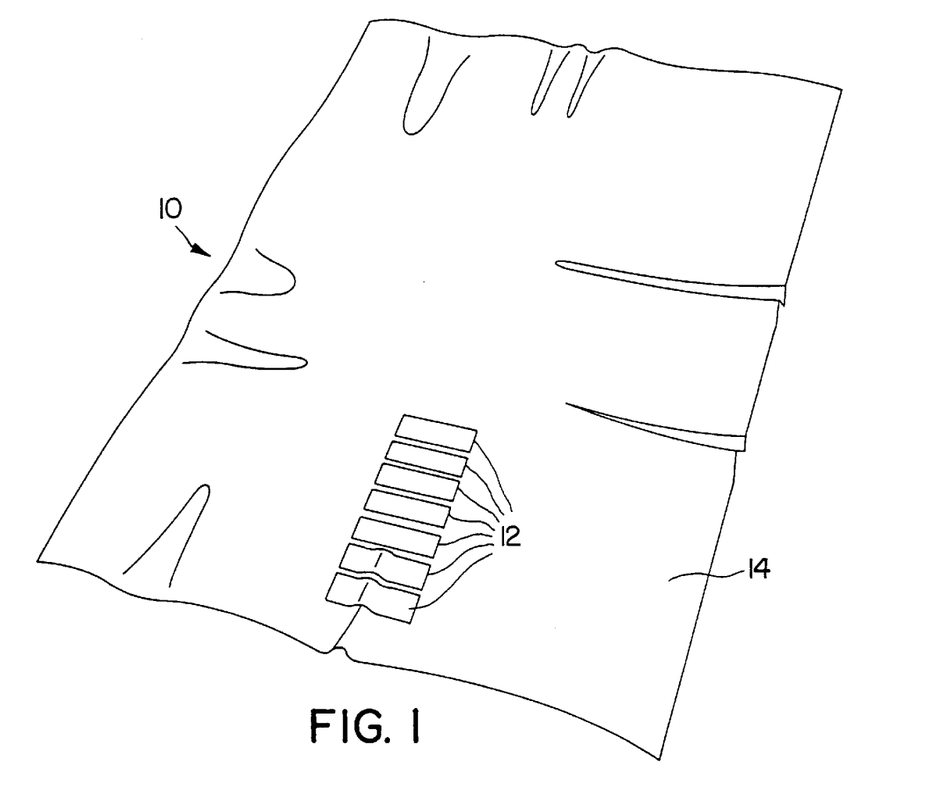
FIG. 1 is a perspective view of a first embodiment of a surgical drape and surgical drape kit according to the present invention showing placement of a number of hook fasteners ready for use.
Figure 2A:
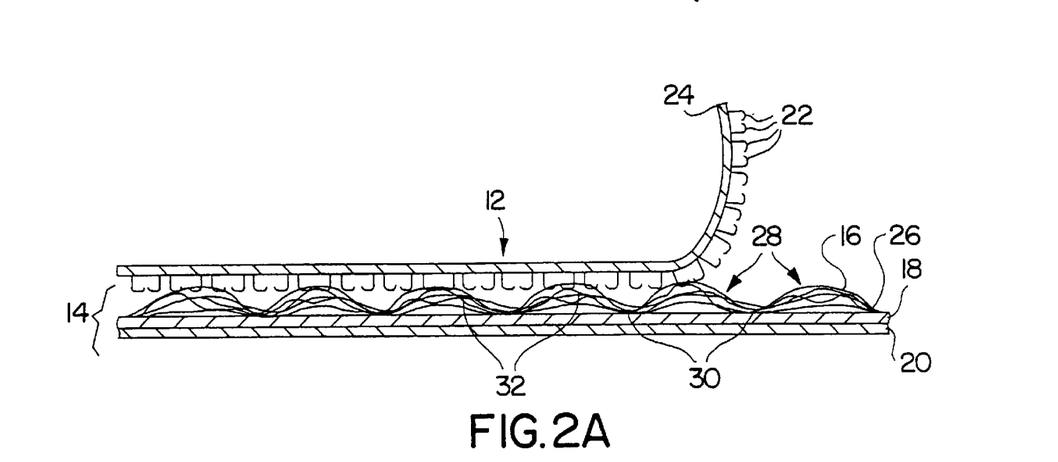
FIG. 2A is a partial sectional view showing the construction of a surgical drape or a portion of a surgical drape according to the present invention having a point bonded surface, and interconnection with one type of hook fastener.
Figure 2B:
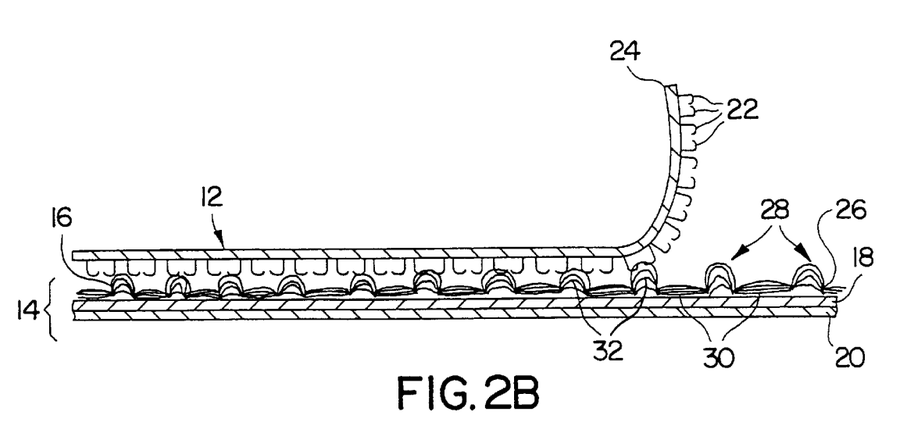
FIG. 2B is a partial sectional view showing the construction of a surgical drape or a portion of a surgical drape according to the present invention having a point unbonded surface and interconnection with one type of hook fastener.

In accordance with the present invention, a first embodiment of a surgical drape according to the invention for engaging a hook fastener to fasten the surgical drape to an object is broadly embodied in FIGS. 1, 2A, and 2B. As shown, surgical drape 10 is provided for engaging hook fasteners 12. Together, surgical drape 10 and hook fasteners 12 may be considered a surgical drape kit, and such a kit may be sold as a unit commercially to ensure that hook fasteners are always provided along with the surgical drape ready for use. If desired, hook fasteners 12 may be sold separately from surgical drape 10 as well.

Surgical drape 10 includes a fabric 14 including at least a nonwoven layer 16. Fabric 14 may have other constructions including additional nonwoven layers, adhesive layers, film layers, etc. Fabric 14 may be constructed so as to be hydrophilic or hydrophobic, and may be chemically treated to achieve the desired water absorbency properties. Preferred constructions of fabric 14 and surgical drapes in general are provided below. As shown in FIGS. 2A and 2B, fabric 14 includes three layers. Nonwoven layer 16 is disposed on one surface of fabric 14 and additional layers 18 and 20 are secured to nonwoven layer 16 in a known way, an example of which is provided below. Layers 18 and 20 impart fluid barrier attributes to drape 10 and may include meltblown or film materials. FIG. 2A broadly depicts a point bonded fabric, and FIG. 2B broadly depicts a point unbonded fabric, both of which are suitable for use in the present invention.

Hook fastener 12 may comprise any sort of hook fastener, as described above, suitable for securing itself to nonwoven layer 16. As shown, hook fastener 12 includes a number of protrusions 22 extending from a backing layer 24. As stated above, protrusions 22 need not have the form of a hook as shown in FIGS. 2A and 2B, but can have various other shapes. The size, shape, and density of protrusions 22 depend on the type of nonwoven layer 16 used and the specific application for the connection between hook fasteners 12 and surgical drape 10.

As shown in FIGS. 2A and 2B, nonwoven layer 16 includes a surface 26 having a plurality of strands 28 arranged on the surface with a plurality of bonds 30 and a plurality of loops 32 extending between the bonds. Loops 32 engage protrusions 22 of hook fasteners 12 to fasten surgical drape 10 to another object. Nonwoven layer 16 may be a point bonded or a point unbonded fabric, may be spunbond or meltblown, or any other nonwoven fabric suitable for use as an upper surface of a surgical drape, as long as it attaches sufficiently to hook fasteners 12.

As shown in FIG. 1, fabric 14 may form substantially all of surgical drape 10. Thus, however many layers are used to construct fabric 14, its cross-section is essentially similar throughout. FIG. 1 shows a surgical drape of uniform construction having a rectangular perimeter, often called a universal drape. Alternately, as will be discussed below, fabric 14 need not comprise the entire surface area of drape 10, but may be applied to a base sheet.

Figure 3:
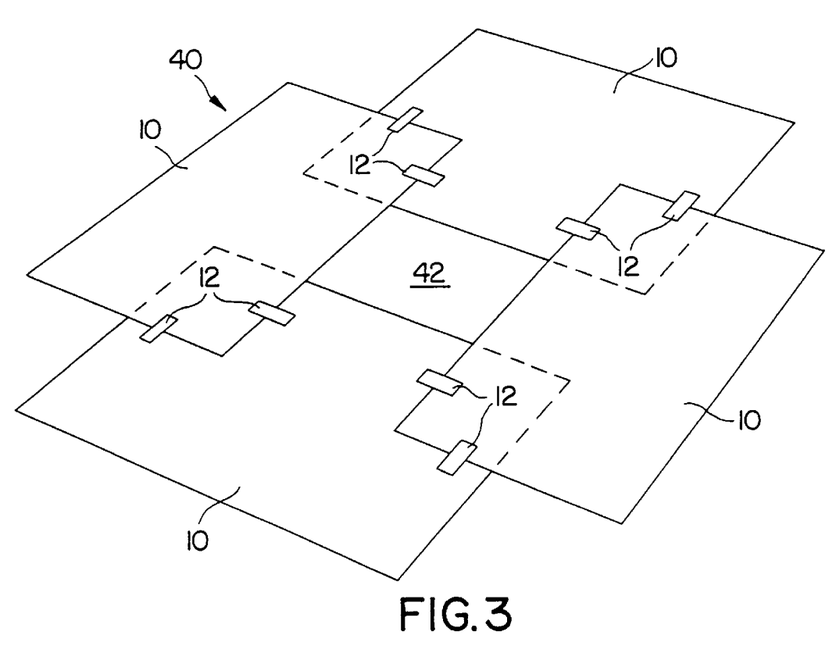
FIG. 3 is a perspective view of a plurality of surgical drapes according to FIG. 1 connected together via hook fasteners to provide a surgical opening.

FIG. 3 broadly shows a surgical drape kit 40 including a plurality of surgical drapes 10. Drape kit 40 may include at least one hook fastener 12 for securing at least two drapes 10 together. As specifically shown in FIG. 3, four drapes 10 and eight hook fasteners 12 are provided. Each drape 10 is secured to two other drapes 10 via two hook fasteners 12 each. Drape kit 40 may include any number of drapes 10 greater than one, and any number of fasteners 12. As shown, the four drapes 10 are arranged so as to define a fenestration opening 42 between the drapes. Such an opening 42 could be created by medical personnel for performing a surgical technique on a patient without the need for a specially-designed drape. Thus, drapes 10 of drape kit 40 could be arranged in any desired manner over the top of a patient and operating table to provide much greater flexibility to the medical personnel. Also, the number of different specific drapes that might need to be purchased and inventoried is reduced through use of drape kit 40.

Hook fasteners 12 of surgical drape kit 40 may either be formed integral with one of the surgical drapes 10, or may be formed separate from all of the surgical drapes. Each hook faster 12 may be formed integral with a surgical drape 10 so as to provide a certain location of the hook fastener. Integral formation can also reduce the amount of time required for medical personnel to set up drape kit 40. However, forming hook fasteners 12 integral with surgical drapes 10 does, at least somewhat, reduce the flexibility provided by drape kit 40.

Figure 4:
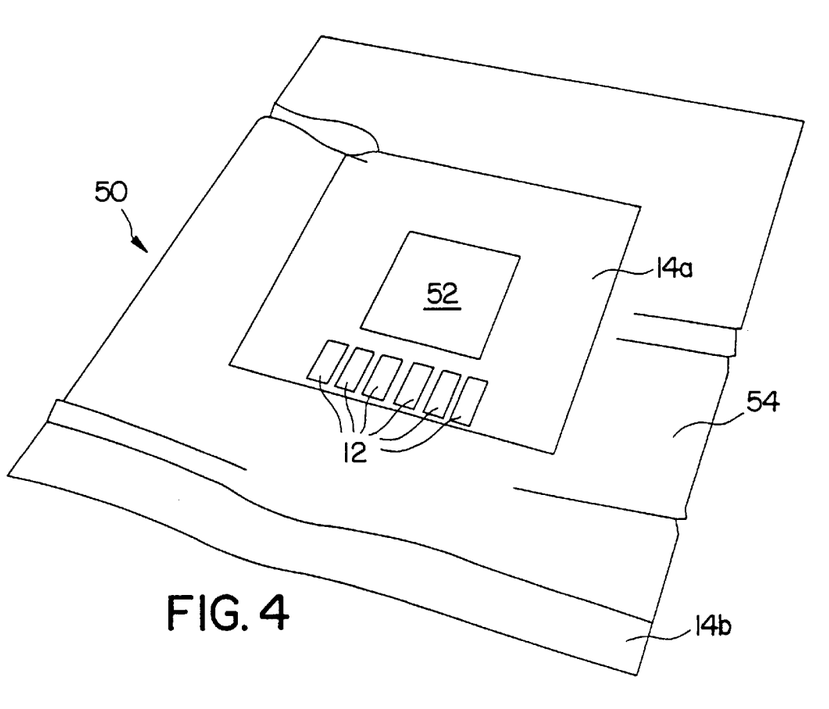
FIG. 4 is a perspective view of a second embodiment of a surgical drape and surgical drape kit according to the present invention showing optional placement of loop material around a fenestration opening and placement of a number of hook fasteners ready for use.

FIG. 4 shows an alternate embodiment of the present invention comprising a surgical drape 50 through which a fenestration opening 52 is provided. Surgical drape 50 is not entirely made of fabric 14, however. Surgical drape 50 includes a base sheet 54 to which a portion of fabric 14a is secured. As shown, fabric 14a covers only a portion of this surface area of base sheet 54. Fabric 14a is engageable with hook fasteners 12, as described above, and the hook fasteners may be provided along with drape 50 to form a surgical drape kit.

As shown in FIG. 4, fabric 14a may be provided adjacent or disposed completely around fenestration opening 52. When used in this location, fabric 14a will preferably be constructed so as to have properties different from fabric 14 when used for an entire drape, as in FIG. 1. For example, large sized drapes that are intended to completely cover the patient yet provide substantial fluid absorption can use a relatively high basis weight, absorbent multilayered nonwoven fabric surrounding the fenestration, while the rest of the drape's base sheet can be relatively low in basis weight and include a barrier such as a film to prevent fluids passing through the drape.

Optionally, an additional portion of fabric 14b may be placed along edge 56 of base sheet 54. Material 14b may be of different construction than material 14a. For example, fabric 14b need not be absorbent or reenforcing, as may be desired for fabric 14a. In any event, fabric 14b can be used along with a hook fastener 12 to secure drape 50 to another drape, surgical table, etc.

Figure 5:
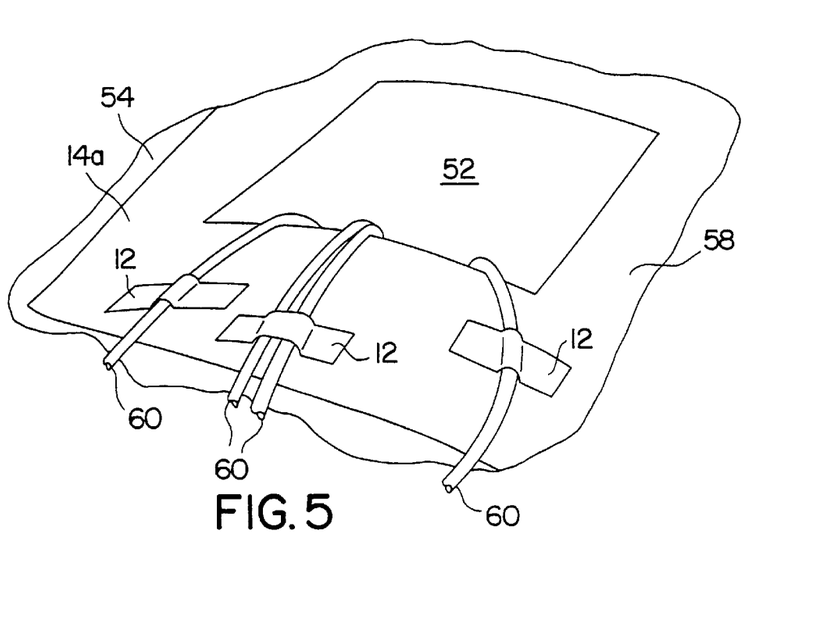
FIG. 5 is a perspective view showing a portion of the surgical drape of FIG. 4 with surgical tools being held in place around the fenestration opening via hook fasteners.

FIG. 5 shows an enlarged view of a surgical drape 50 according to FIG. 4 in use. A reinforcement 58 may border at least one edge of or extend around all edges of fenestration opening 52 to provide a defined area that has functional attributes in addition to that of fluid barrier, such as high absorption capacity (relative to the drape's base sheet), a slip resistant surface for placement of medical instruments, or fastening ability. As shown, a plurality of surgical tools 60 are secured to fabric 14a of drape 50 via hook fasteners 12. Surgical tools 60 are essentially infinitely positionable and repositionable on fabric 14a, limited only by the size of fabric 14a, fenestration opening 52, and hook fasteners 12, etc.

As shown in FIGS. 4 and 5, hook fasteners 12 are formed separate from surgical drape 10. However, if desired, hook fasteners 12 may be formed integral with the surgical drape, as demonstrated by the embodiment of the invention shown in FIGS. 6 and 7. As shown therein, a surgical drape 70 includes a nonwoven fabric 14c secured to a base sheet 72. Fabric 14c includes at least one slit 74 defining at least one tab 76 having a distal end 78 extending from the rest of the fabric. Hook fastener material 80 is disposed on each tab 76 for engaging a portion of fabric 14c. Distal end 78 may also include an end portion 82 where no hook fastener 80 material is present to provide for easy gripping, especially for unattaching hook fastener 80 from fabric 14c.

Figure 6:
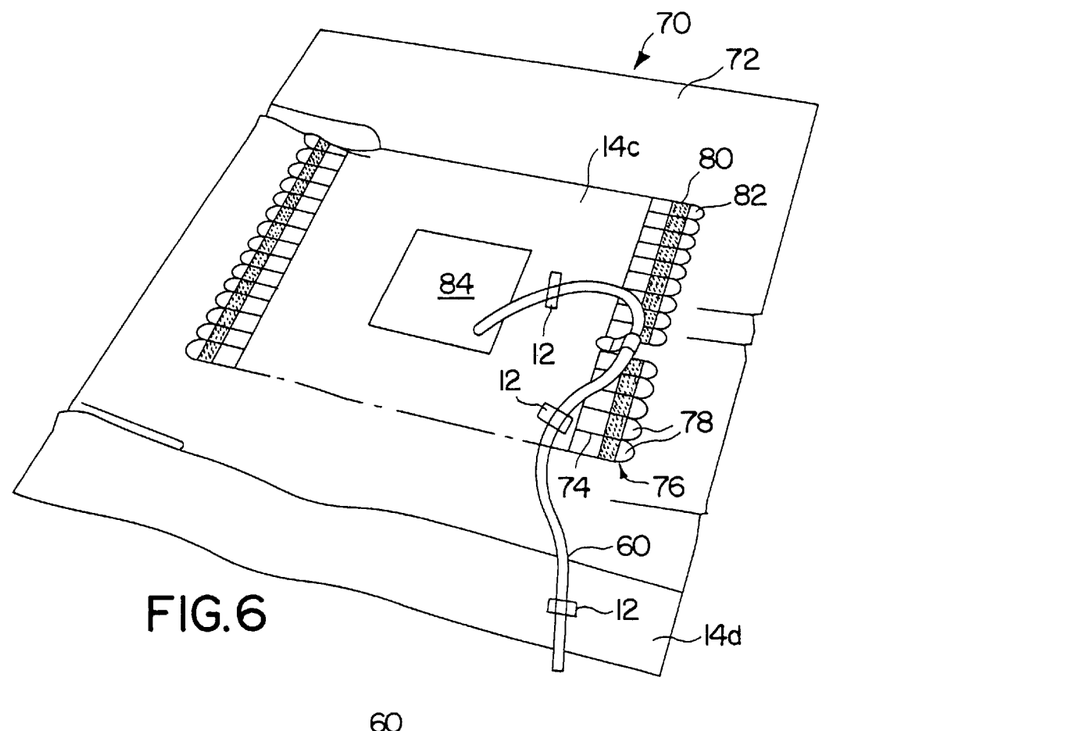
FIG. 6 is a perspective view of a third embodiment of the present invention showing optional placement of loop material and hook material on tabs disposed around a fenestration opening for holding a surgical tool, and also showing optional placement of loop material along an edge of the surgical drape.
Figure 7:
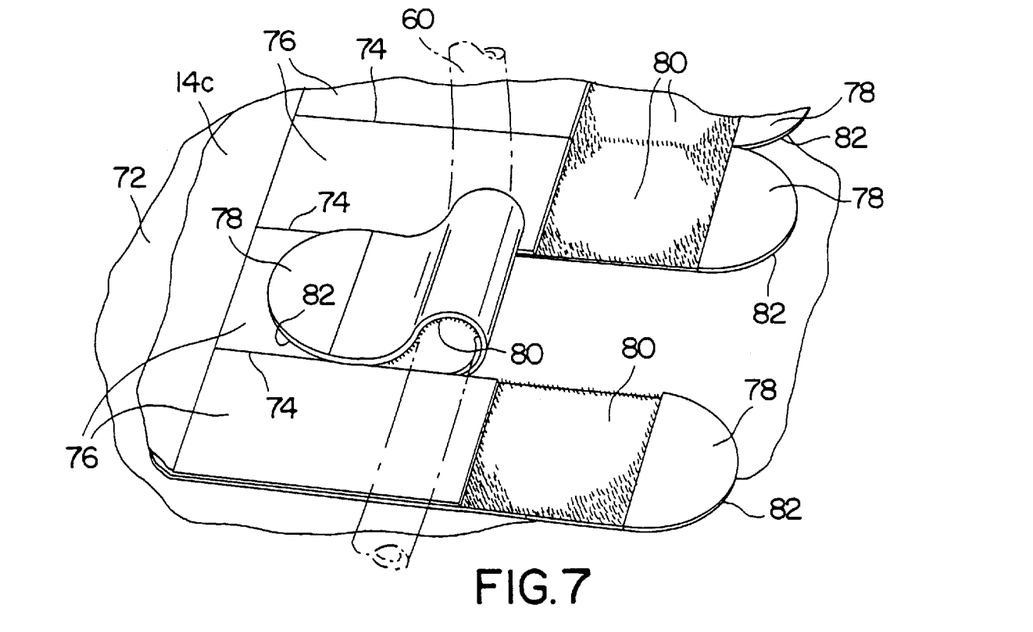
FIG. 7 is a perspective view of several of the tabs of the surgical drape of FIG. 6 showing details of the tabs and how they hold the surgical tool in place.

As shown in FIG. 7, hook fastener material 80 may be attached to an inner portion of its tab 76 or an adjacent tab 76. Alternately, tab 76 may be folded over far enough that hook fastener material 80 attaches to a portion of fabric 14c past the ends of slits 74. Optionally, as shown in FIG. 6, additional hook fasteners 12 may be provided, apart from tabs 76, for further securing a surgical tool 60 to portion 14c.

Also, fabric 14d may be provided for further securing a surgical tool or another object to drape 70. As shown in FIG. 6, fabric 14c including tab 76 is provided around a fenestration opening 84, but it would also be possible to place tabs 76 according to FIG. 7 on other fabric portions on other drapes, such as fabric portion 14b or 14d.

Although various materials are suitable for use as the drape, base sheet, fabric, and hook fasteners described above, applicants have identified some preferred combinations of materials. These combinations, which should not be construed as limitations on the claimed invention, are set forth below.

For example, for drapes according to FIG. 1, each drape may consist of a nonwoven surface layer joined to a barrier layer by a meltblown adhesive layer. The nonwoven surface layer may be a spunbond fabric of about 2.0 denier filaments (strands) made from a copolymer of propylene with 3.5% ethylene (Union Carbide 6D43 from Union Carbide Corp.), having a basis weight of 20 grams per square meter (gsm), and having been bonded by a repeating pattern of discretely fused areas spaced apart to give 111 fused areas per square inch and a 17.7% total bonded area.

The meltblown adhesive layer may be made from an amorphous polyolefin (Rextac 2730 from Huntsman Corporation), and it is applied to the spunbond surface at 3 gsm.

The barrier layer is a film made of 47% linear low density polyethylene (Dowlex NG 3310 available from Dow Chemical Co.), 48% Supercoat™ (a ground, stearic acid coated calcium carbonate available from English China Clay), and 5% low density polyethylene (Dow 4012 available from Dow Chemical Co.) The initial thickness of the film should be 1.5 mil. The film is stretched 4X in one direction just prior to lamination to the spunbond by the meltblown adhesive layer. The film provides an impermeable barrier to aqueous fluids and alcohol solutions; the inclusion of the calcium carbonate and subsequent stretching of the film prior to lamination improves moisture vapor permeability.

The drapes made according to the above construction have a 51 gsm basis weight, a water vapor transmission rate of 2429 grams per square meter per 24 hours. The spunbond may be treated to be hydrophilic.

The type of hook fastening strips used to secure the drapes together is preferably Velcro 51-1003. The strips are preferably 12 cm×4.5 cm. In the longest direction, the ends of the strips preferably do not engage the nonwoven surface (the hooks are blunted back −1 cm from the end) to allow manipulation in placement and repositioning.

Another drape construction could be used for a general surgery drape having a centrally positioned fenestration including an attached multilayer fabric that surrounds the fenestration, as shown in FIG. 4. This multilayer fabric contains a fluid barrier layer, absorbent layers to control fluids present during the operation, and a nonwoven surface layer that readily engages with a hook fastening strip. This system (multilayer fabric around the fenestration and the hook fastening strips) performs the same fluid control function typical of fenestration reinforcement fabrics and eliminates the need of tube holders and other cumbersome attachment devices for positioning surgical tool cords and tubes.

The drape is preferably made from a 193 cm×305 cm nonwoven laminate made of polypropylene spunbond and meltdown layers according to U.S. Pat. No. 4,041,203, incorporated by reference herein. A 10 cm×30.5 cm fenestration is centrally positioned. Around the fenestration is a multilayered fabric having exterior dimensions of 65 cm×100 cm that consists of a bottom film layer, a center 34 gsm hydrophilic meltblown layer, and a 64 gsm hydrophilic spunbond surface layer that has continuous bond areas that define a plurality of discrete unbonded areas, which are suitable for engaging hook fasteners.

The spunbond fabric is formed from two layers of multicomponent filaments made according to U.S. Pat. No. 5,418,045, incorporated by reference herein, and bonded so that a plurality of discrete unbonded circular areas of ~0.4 cm are spaced ~0.5 cm apart in a hexagonal (close packing) arrangement. The upper surface of the spunbond fabric may be composed of 9 denier filaments (circular in cross-section and having polymeric components arranged in a side-by-side configuration of a) Exxon 3445 polypropylene and b) Dow's ASPUN 6811A linear low density polyethylene, both at 49% by weight with the remainder being titanium dioxide pigment). The lower layer of spunbond may be composed of 2 denier filaments having the same composition as the 9 denier filaments. Total bond area is 15%. The fabric may be made wettable by treatment with a surfactant in the manner described in U.S. Pat. No. 5,540,979, incorporated by reference herein. The meltblown layer is preferably made of polypropylene, is made hydrophilic as described in U.S. Pat. No. 5,540,979, and preferably has a basis weight of 34 gsm. The barrier layer is preferably a 1 mil film, Code XXII Blue 246 from Clopay Corp. All layers of the multicomponent fabric are thermally laminated together using discrete bond points as described in U.S. Pat. No. 5,540,979. The multilayer fabric is adhesively laminated to the base sheet using an aqueous adhesive (L 8052-01 from Findley Adhesives). Hook fastening strips of 12 cm×5 cm, preferably 3M's XKH-7163A, may be used to secure surgical tools to the drape.

Among the surgical tools and their components for which this fastening system is especially well suited are: fiber optical cords, endoscopic tubing, cords for cauterizing pencils, smoke evacuator tubing, and irrigation/aspiration tubing.

An alternate surgical drape construction combining the above examples has a fenestration and fabric reinforcement around the fenestration and allows for hook fastening strips to be attached anywhere on the drape's surface. The fabric described in embodiment 1 (nonwoven/film construction) may form the base sheet of the drape. The fabric surrounding the fenestration as described in embodiment 2 may be attached to the base sheet. The result is a drape that allows surgical tools (i.e. cords and tubing) to be secured near the fenestration using strips of hook fasteners and allows for the base sheet of the drape to be shaped/gathered around supporting framework (e.g. U-bars) and/or the patient and held in position by the attachment of hook fastening strips to the exposed drape surfaces.

For drapes containing a fastening system that has a hook fastening strip integrated into the drape body as in FIGS. 6 and 7, the barrier film of the multilayer fabric surrounding the fenestration described above related to the drape of FIG. 4 extends beyond the edge of the meltblown and spunbond layers by 7 cm on opposing sides and is unattached to the base sheet. Attached at the edge of the film are aligned 2.5 cm×4.5 cm hook fastening strips, these strips are positioned so that the 4.5 cm dimensions section the edge of the unattached film. The strips are set back 0.5 cm from the film edge (to facilitate manipulation and attachment of the hook fastening strip). The nonwoven surface fabric is the same as described for the drape of FIG. 4. The hook fastening strips are Velcro 51-1004; they are attached to the film using an adhesive such as an aqueous adhesive (L 8052-01 from Findley Adhesives).

Applicants have performed testing to determine desirable lower limits for engagement between a hook fastening strip and a drape surface to securely fasten surgical tools in a quick and convenient manner.

The following Tables summarize tests of examples made according to the present invention and compare results using the examples made according to the present invention to other materials. In the Tables, the Hook Peel Strength and Hook Shear Strength values, measured according to the test methods set forth above, are listed for combinations of various hook fasteners and various nonwoven surgical drape materials. Hook Peel Strength and Hook Shear Strength are measured between hook fastening strips and samples of nonwoven fabrics used as surgical drapes cut with respect to the nonwoven fabric's machine direction (MD) and the cross machine direction (CD). Average values (AVE) for peel and shear measurements are then determined as the mean of the MD and CD values.

The nonwoven fabrics consisted of:

Fabric 1—20 gsm spunbond laminated to film via meltblown hot melt adhesive (Example 1)

Fabric 2—64 gsm spunbond with continuous bond areas thermally point bonded to 34 gsm meltblown bonded in turn to film (Example 2)

Fabric 3—54 gsm spunbond/meltblown/spunbond used in Kimberly-Clark Corp.'s utility drapes (Component Stock # 79731)

Fabric 4—102 gsm Control Plus® fabric reinforcement made by Kimberly-Clark Corp.

Fabric 5—nonwoven drape fabric from Barrier Hip Sheet with Side Pocket (Sterile Code 0204), made by Johnson & Johnson Medical, Inc. of Arlington, Texas.

TABLE 1

Hook component: XKH-7163A fastener (~211 hooks/cm$^2$),
available from 3M Corp.

| Fabric | Hook Peel MD | (gm) CD | AVE | Hook Shear MD | (gm) CD | AVE |
|---|---|---|---|---|---|---|
| 1 | 119 | 99 | 109 | 3750 | 3246 | 3498 |
| 2 | 373 | 331 | 352 | 4624 | 4427 | 4526 |
| 3 | 20 | 15 | 18 | 1025 | 500 | 763 |
| 4 | 69 | 47 | 58 | 2064 | 1751 | 1908 |
| 5 | no attachment | no attachment | — | no attachment | no attachment | — |

TABLE 2

Hook component: 51-1004 fastener (~333.5
hooks/cm$^2$), available from Velcro International.

| Fabric | Hook Peel MD | (gm) CD | AVE | Hook Shear MD | (gm) CD | AVE |
|---|---|---|---|---|---|---|
| 1 | 138 | 165 | 152 | 3393 | 2891 | 3142 |
| 2 | 423 | 623 | 523 | 6928 | 5995 | 6462 |
| 3 | 15 | 17 | 16 | 127 | 104 | 116 |
| 4 | 69 | 117 | 93 | 947 | 1685 | 1316 |
| 5 | no attachment | no attachment | — | 27 | 23 | 25 |

TABLE 3

Hook component: Hook fastening strip included as an attached
component to Johnson & Johnson's Barrier Hip Sheet with Side
Pocket (Sterile Code 0204) drape kit (~111 hooks/cm$^2$).

| Fabric | Hook Peel MD | (gm) CD | AVE | Hook Shear MD | (gm) CD | AVE |
|---|---|---|---|---|---|---|
| 1 | 53 | 29 | 41 | 119 | 55 | 87 |
| 2 | 473 | 323 | 398 | 1275 | 1426 | 1351 |
| 3 | no attachment | no attachment | — | 26 | 28 | 27 |
| 4 | 91 | 38 | 65 | 77 | 28 | 53 |
| 5 | no attachment | no attachment | — | 12 | 24 | 18 |

As shown by each of the Tables, for a given hook fastening strip, Fabrics 1 and 2 (corresponding to Examples 1 and 2) measurably engage to a greater degree than nonwoven fabrics that are traditionally bonded and laminated. Tables 1 and 2 show preferred hook fastening strips having more than 200 hooks per square cm useful with nonwovens. Table 3 shows a hook fastening strip usually used for attaching to woven fabric surfaces (this strip is designed to engage a specific woven loop material that is affixed to the drape's surface in predetermined areas), but that is suitable for use with at least some fabrics according to the present invention.

Lower limits (based on the values in the Tables) for achieving secure, but "repositionable," attachment of medical devices to a nonwoven intended as the surface of a drape can be determined when associated with "attachment" scenarios consisting of: securing a one meter segment of flexible PVC tubing (suction tubing, ¼ inch inside diameter, durometer hardness of 65, part number 9036290, from Davoll, subsidiary of C. R. Bard, Inc.) between the ends of a 2.5 cm×4.5 cm hook fastening strip to a nonwoven fabric, and then pulling on the tubing in various direction to qualitatively assess attachment between the strip and the fabric.

Such assessments showed that the tubing was best secured using the following hook fastening strip and fabric combinations: the hook fastening strips of Tables 1 and 2 when engaged to Fabrics 1 and 2, and the hook fastening strip of Table 3 when engaged to Fabric 2. For all the other combinations of hook fasteners and nonwoven fabrics the movement of the tubing easily disengaged the hook fastening strip from the nonwoven, and were thus judged unsatisfactory.

By comparing the Hook Peel and Hook Shear Strength values for those hook fastening strip and nonwoven fabric combinations that gave secure attachment of the tubing to the values of the hook fastening strip and nonwoven fabric combinations that did not give secure attachment, a preferred lower limit of attachment is determined. Some combinations provided acceptable Hook Shear Strength but unacceptable Hook Peel Strength. In order to be useful, a combination must have acceptable performance in both tests.

Based on measurements listed above and averaging of acceptable MD and CD measurements, it is estimated that minimum acceptable Hook Peel Strength (for the size fasteners tested) is about 100 g, and a more preferable minimum amount is about 110 g. Similarly, a minimum acceptable Hook Shear Strength (for the size fasteners tested) is about 1350 g, and a more preferable minimum amount is about 2000 g. The measurements of fabrics 1 and 2 fall within or near these ranges, and the measurements of fabrics 3–5 fall outside these ranges (keeping in mind that an acceptable fabric must fall within preferred ranges for both peel and shear).

It will be apparent to those skilled in the art that various modifications and variations can be made in the present invention without departing from the scope and spirit of the invention. It is intended that the present invention include such modifications and variations as come within the scope of the appended claims and their equivalents.

What is claimed is:

1. A surgical drape comprising:
   a fabric including a nonwoven layer, the nonwoven layer having a surface including a plurality of strands, the strands being arranged on the surface with a plurality of bonds spaced about the surface and a plurality of loops extending between the bonds; and
   a hook fastener formed integral with the fabric and including a plurality of hooks for engaging the loops for fastening the surgical drape to an object.

2. The surgical drape of claim 1, wherein the fabric forms substantially the entire surgical drape.

3. The surgical drape of claim 1, the surgical drape further including a base sheet, the fabric being secured to the base sheet.

4. The surgical drape of claim 3, wherein the base sheet defines a surface area and the fabric covers only a portion of the surface area.

5. The surgical drape of claim 3, wherein the base sheet defines an edge, the fabric being disposed adjacent the edge.

6. The surgical drape of claim 3, wherein the base sheet defines a fenestration opening, the fabric being disposed adjacent the fenestration opening.

7. The surgical drape of claim 3, wherein the base sheet defines a fenestration opening, the fabric being disposed around the fenestration opening.

8. The surgical drape of claim 1, wherein the nonwoven layer includes a spunbond material.

9. The surgical drape of claim 1, where in the nonwoven layer includes a meltblown material.

10. The surgical drape of claim 1, wherein the other object is a surgical tool.

11. The surgical drape of claim 1, wherein the other object is a second surgical drape.

12. The surgical drape kit of claim 1, wherein the hook fastener peel strength is 100 g or more.

13. The surgical drape kit of claim 1, wherein the hook fastener peel strength is 110 g or more.

14. The surgical drape kit of claim 12, wherein the hook fastener shear strength is 1350 g or more.

15. The surgical drape kit of claim 1, wherein the hook fastener shear strength is 2000 g or more.

16. The surgical drape of claim 1, wherein the fabric includes at least one slit defining at least one tab having a distal end extending from the fabric, the hook fastener being disposed adjacent the distal end of the tab.

17. The surgical drape kit of claim 16, wherein the surgical drape kit includes a plurality of the tabs.

18. The surgical drape of claim 1, wherein the fabric is hydrophilic.

19. The surgical drape of claim 1, wherein the fabric is absorbent.

20. A surgical drape for engaging a hook fastener to fasten the surgical drape to an object, the surgical drape comprising:

a base sheet defining a fenestration opening; and a reinforcing fabric secured to the base sheet adjacent the fenestration opening, the reinforcing fabric including a nonwoven layer, the nonwoven layer having a surface including a plurality of strands, the strands being arranged on the surface with a plurality of bonds spaced about the surface and a plurality of loops extending between the bonds, the loops being engageable with the hook fastener for fastening an object to the reinforcing fabric.

21. The surgical drape of claim 20, wherein the reinforcing fabric is disposed around the fenestration opening.

22. The surgical drape of claim 20, wherein the nonwoven layer includes a spunbond material.

23. The surgical drape of claim 20, where in the nonwoven layer includes a meltblown material.

24. The surgical drape of claim 20, wherein the other object is a surgical tool.

25. The surgical drape of claim 20, wherein the hook fastener is formed integral with the reinforcing fabric.

26. The surgical drape of claim 20, wherein the hook fastener is formed separate from the reinforcing fabric.

27. The surgical drape of claim 20, wherein the base sheet includes a nonwoven fabric having a first basis weight and the nonwoven layer of the reinforcing fabric has a second basis weight higher than the first basis weight.

28. The surgical drape of claim 20, wherein the surface of the nonwoven layer of the reinforcing fabric is slip resistant.

29. The surgical drape of claim 20, wherein the reinforcing fabric is hydrophilic.

30. The surgical drape of claim 20, wherein the reinforcing fabric has an absorbency higherr than that of the base sheet.

* * * * *